(12) United States Patent
Paulk et al.

(10) Patent No.: US 9,314,240 B2
(45) Date of Patent: Apr. 19, 2016

(54) LOCKING SUTURE ANCHOR ASSEMBLY

(75) Inventors: David A. Paulk, Hopedale, MA (US); Richard Mark Lunn, Kingston, MA (US)

(73) Assignee: Smith & Nephew, Inc., Memphis, TN (US)

( * ) Notice: Subject to any disclaimer, the term of this patent is extended or adjusted under 35 U.S.C. 154(b) by 914 days.

(21) Appl. No.: 13/509,167

(22) PCT Filed: Nov. 10, 2010

(86) PCT No.: PCT/US2010/056160
§ 371 (c)(1),
(2), (4) Date: Sep. 6, 2012

(87) PCT Pub. No.: WO2011/060022
PCT Pub. Date: May 19, 2011

(65) Prior Publication Data
US 2013/0006302 A1    Jan. 3, 2013

Related U.S. Application Data

(60) Provisional application No. 61/259,732, filed on Nov. 10, 2009.

(51) Int. Cl.
*A61B 17/04* (2006.01)
*A61B 17/86* (2006.01)

(52) U.S. Cl.
CPC ........... *A61B 17/0401* (2013.01); *A61B 17/864* (2013.01); *A61B 2017/0409* (2013.01); *A61B 2017/0414* (2013.01); *A61B 2017/0427* (2013.01); *A61B 2017/0437* (2013.01); *A61B 2017/0441* (2013.01); *A61B 2017/0445* (2013.01); *A61B 2017/0453* (2013.01)

(58) Field of Classification Search
USPC ...................... 606/232, 246, 139, 104, 63, 60
See application file for complete search history.

(56) References Cited

U.S. PATENT DOCUMENTS

| 4,738,255 | A | 4/1988 | Goble et al. |
| 5,152,790 | A | 10/1992 | Rosenberg et al. |
| 5,464,427 | A | 11/1995 | Curtis et al. |
| 7,329,272 | B2 | 2/2008 | Burkhart et al. |
| 7,678,134 | B2 * | 3/2010 | Schmieding et al. ......... 606/232 |

(Continued)

FOREIGN PATENT DOCUMENTS

| EP | 0673624 A2 | 9/1995 |
| JP | 2000-512193 A | 9/2000 |

(Continued)

OTHER PUBLICATIONS

Second Office Action for Chinese Application No. 201080050979.3, issued Nov. 14, 2014.

(Continued)

*Primary Examiner* — Vy Bui
(74) *Attorney, Agent, or Firm* — Burns & Levinson LLP; Joseph M. Maraia

(57) ABSTRACT

The present disclosure relates to an anchor assembly. The anchor assembly includes an anchor including a distal portion and a proximal portion, the anchor defining a cavity and an opening to the cavity; an insertion member disposed within the cavity of the anchor; and a sleeve coupled to the anchor, the sleeve disposed over the proximal portion of the anchor. A delivery device is also disclosed.

7 Claims, 7 Drawing Sheets

(56) References Cited

U.S. PATENT DOCUMENTS

| | | | |
|---|---|---|---|
| 8,454,654 B2* | 6/2013 | Ferragamo et al. | 606/232 |
| 9,179,907 B2 | 11/2015 | Elattrache et al. | |
| 2002/0013608 A1 | 1/2002 | Elattrache et al. | |
| 2004/0138706 A1 | 7/2004 | Abrams | |
| 2004/0225292 A1 | 11/2004 | Sasso et al. | |
| 2006/0246396 A1* | 11/2006 | Suttin et al. | 433/173 |
| 2006/0271060 A1 | 11/2006 | Gordon | |
| 2008/0009904 A1 | 1/2008 | Bourque | |
| 2009/0112270 A1 | 4/2009 | Lunn et al. | |
| 2009/0157124 A1 | 6/2009 | Ferragamo et al. | |

FOREIGN PATENT DOCUMENTS

| | | |
|---|---|---|
| JP | 2005-504555 A | 2/2005 |
| JP | 2006-95301 B2 | 4/2013 |
| WO | 9842261 A1 | 10/1998 |
| WO | 0243576 A2 | 6/2002 |
| WO | 2009055800 A1 | 4/2009 |

OTHER PUBLICATIONS

Patent Examination Report No. 1 for Australian Application No. 2010319662, issued Feb. 11, 2015.
Office Action for Russian Application No. 2012122881/14(034786), mailed Dec. 1, 2014.
Notice of Reasons for Rejection for Japanese Application No. 2012-538929, mailed Jul. 22, 2014.
First Office Action for Chinese Application No. 201080050979.3, issued Jun. 5, 2014.
Third Office Action for Chinese Application No. 201080050979.3, issued Apr. 24, 2015.
Patent Examination Report No. 2 for related Australian Patent Application No. 2010319662 mailed Sep. 18, 2015.
Decision of Rejection for Japanese Application No. 2012-538929, mailed Apr. 6, 2015.
Office Action for Russian Application No. 2012122881/14(034786), mailed Mar. 18, 2015.

* cited by examiner

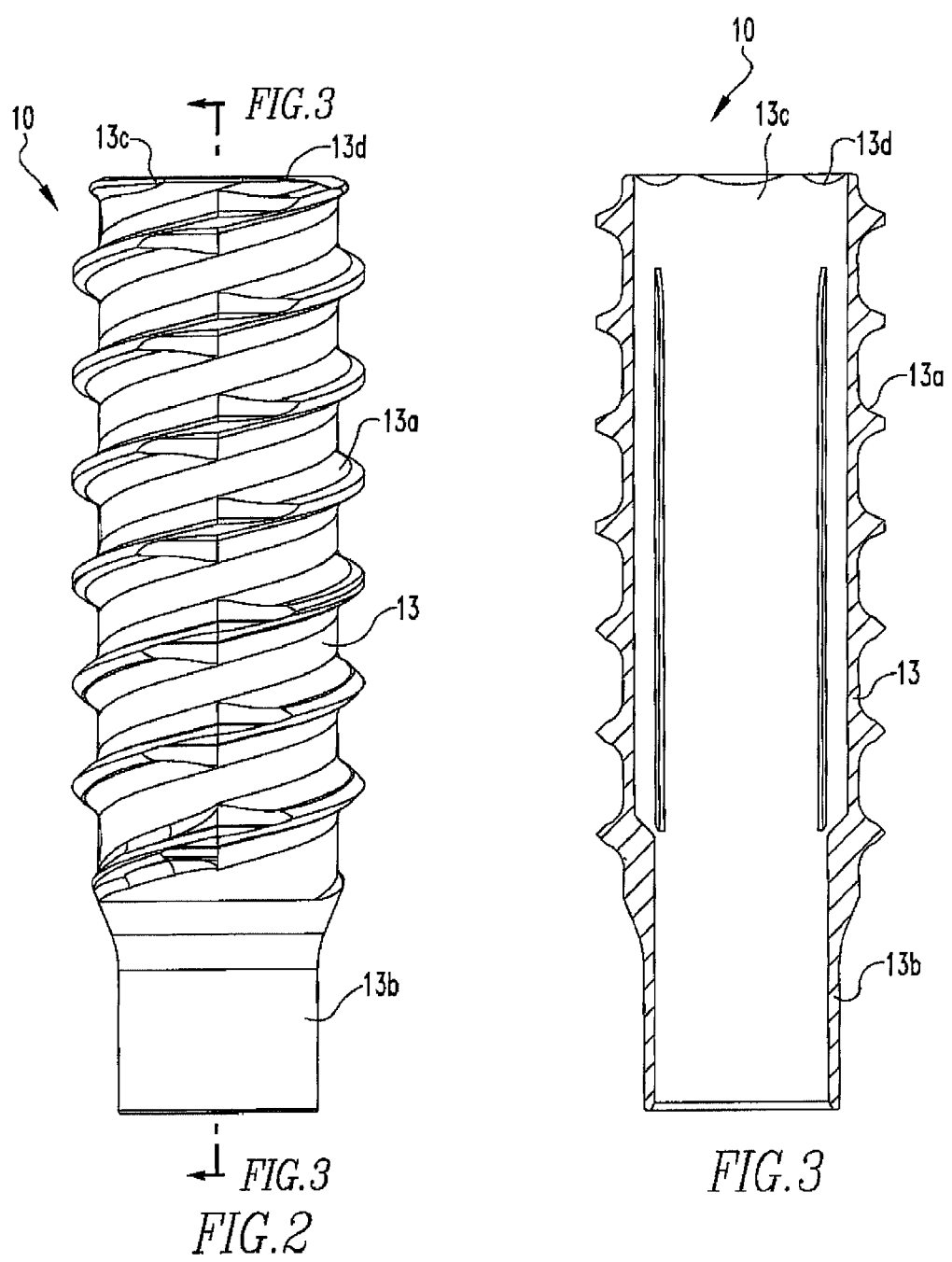

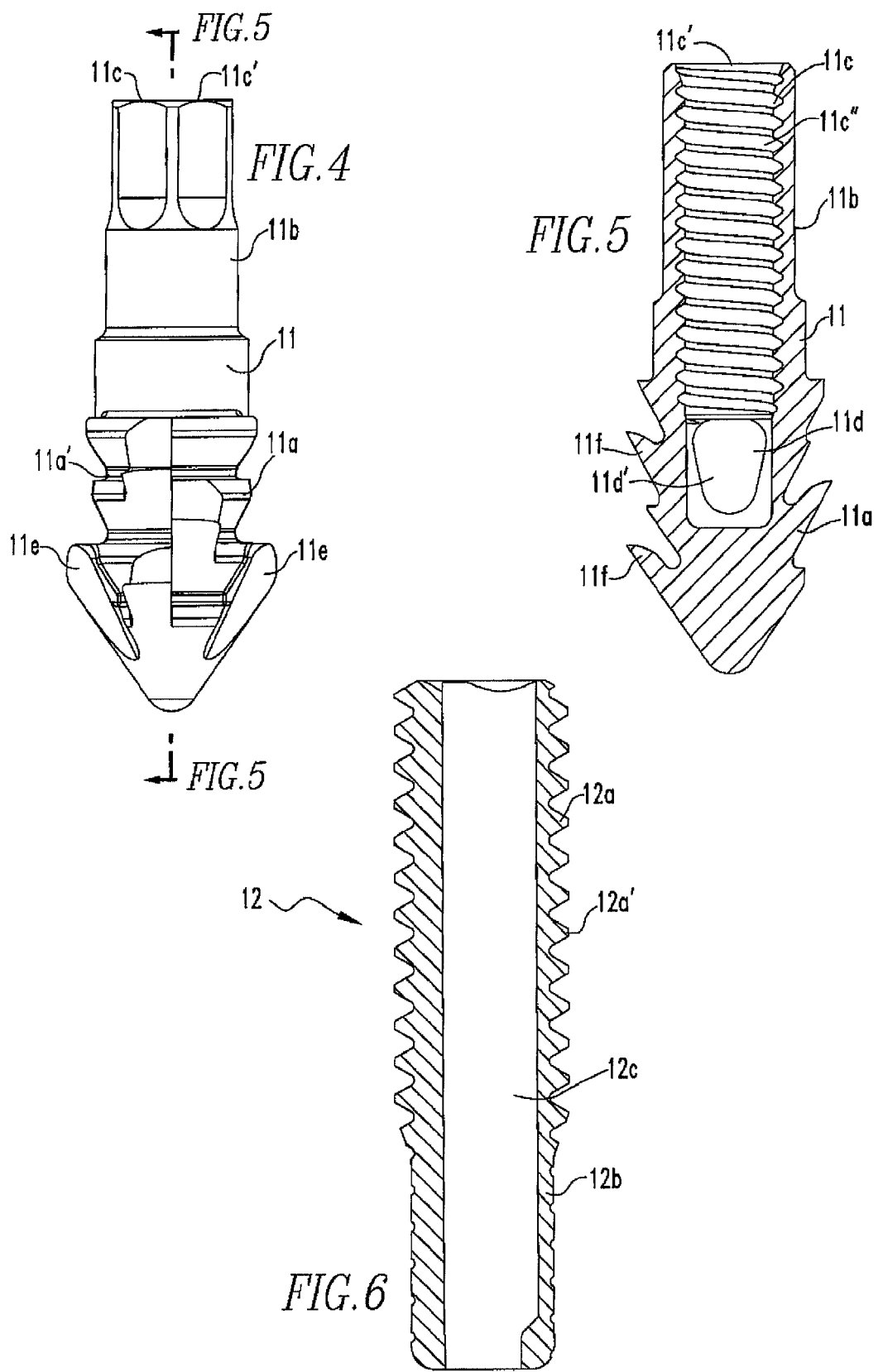

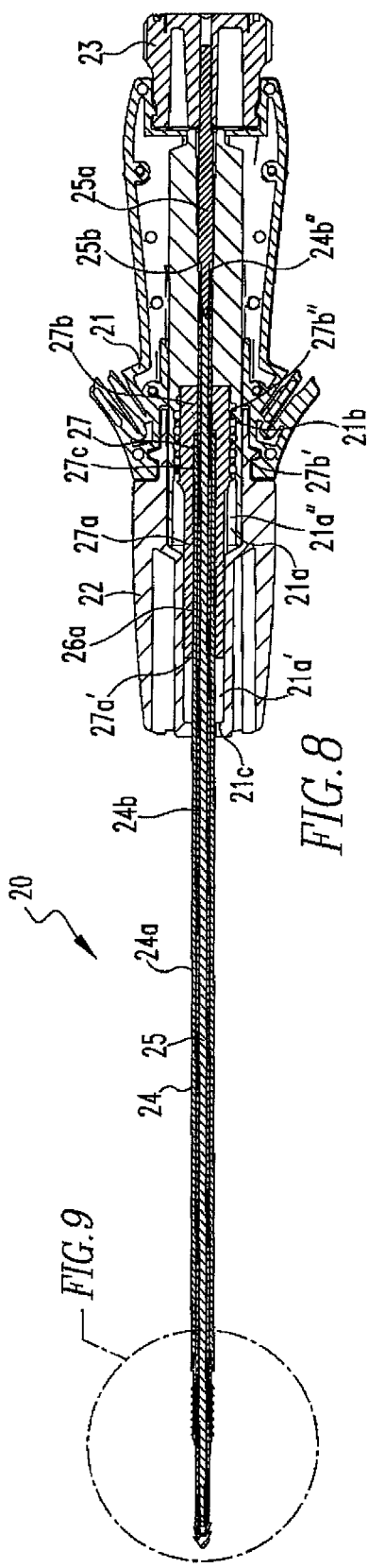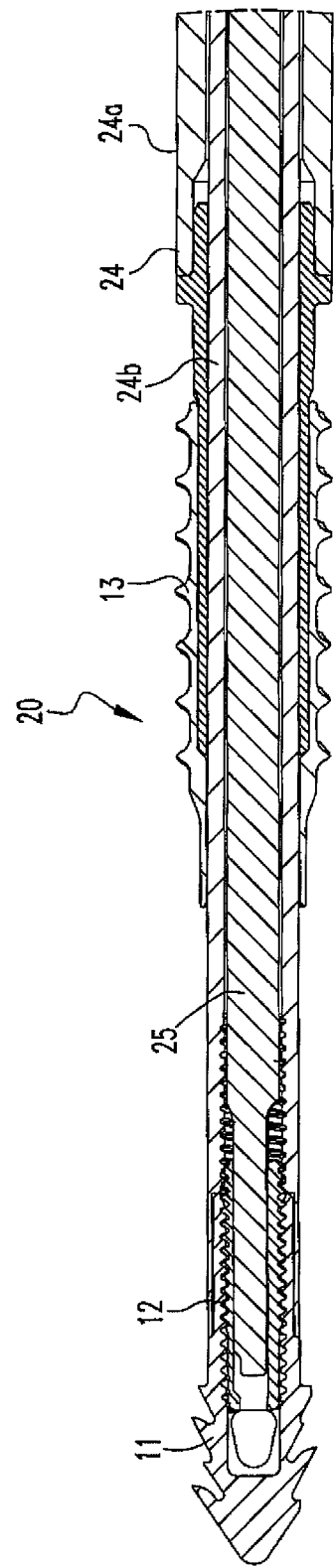
FIG.8
FIG.9

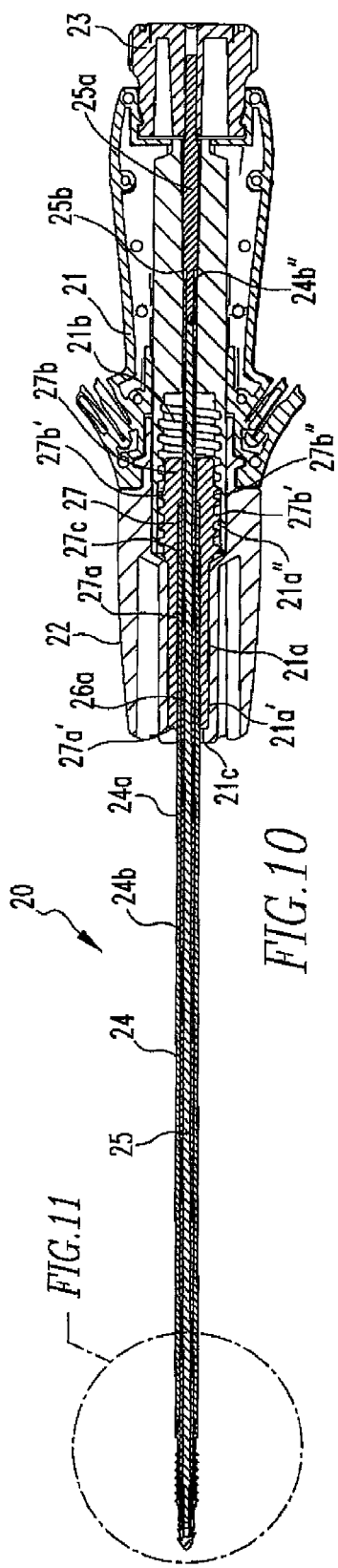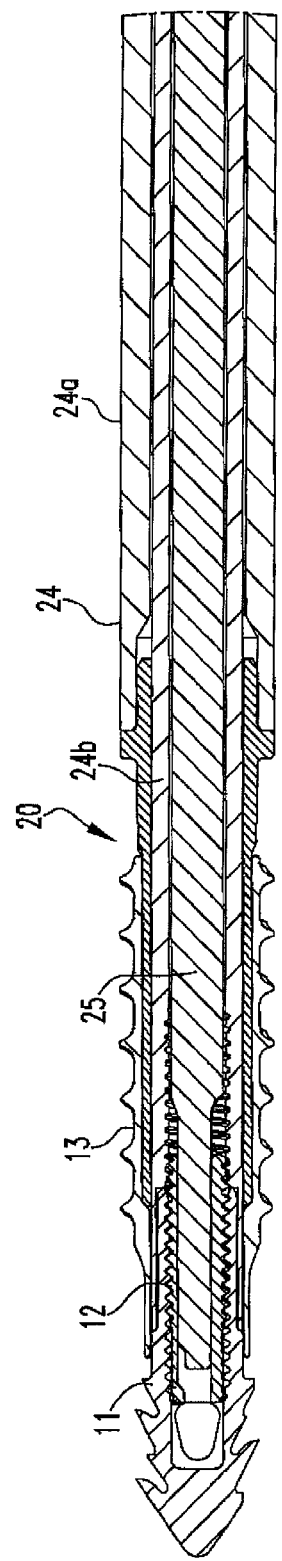

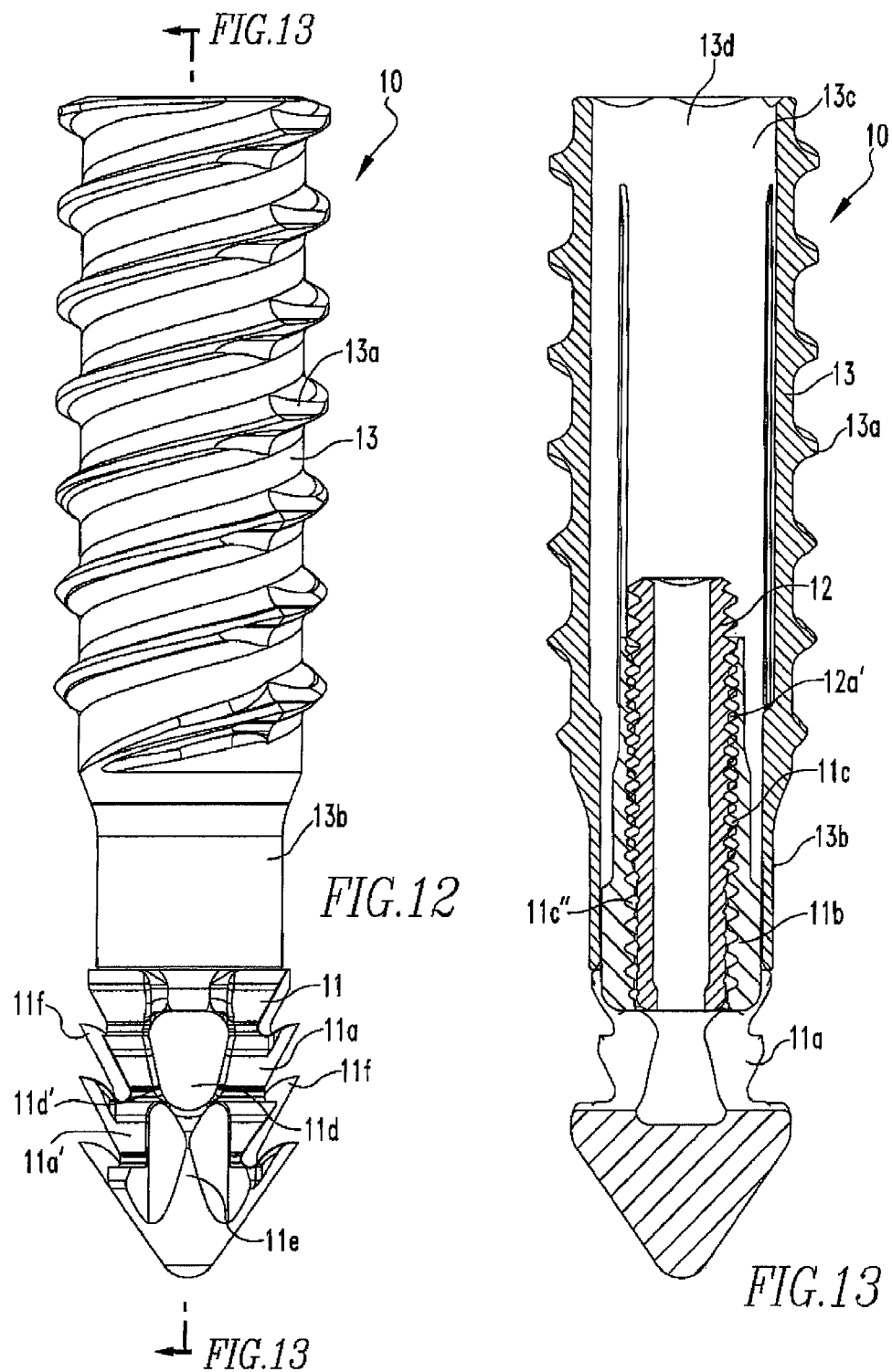

LOCKING SUTURE ANCHOR ASSEMBLY

CROSS-REFERENCE TO RELATED APPLICATIONS

This application is a national stage application of PCT/US2010/056160, filed Nov. 10, 2010 which claims priority to U.S. Patent Application No. 61/259,732 filed on Nov. 10, 2009, the disclosures of which are incorporated herein by reference in their entireties.

BACKGROUND OF THE INVENTION

1. Field of the Invention

The present disclosure relates to tissue repair, and more specifically, to an anchor for securing tissue to bone.

2. Related Art

Arthroscopic procedures often require soft tissue to be reattached to bone. To achieve this, anchors are placed in the bone and sutures attached to the anchor are passed through the tissue to securely retain the tissue in place. When making a repair of soft tissue to bone, it is advantageous to have as large an area of contact between the bone and tissue as possible. Anchor points spaced from one another in rows result in a repair having a broader area of contact. A procedure, and components for use in such procedure, that securely attaches tissue to bone using a plurality of attachment points over a large area of contact is needed. Such procedure must be able to be done in a quick and efficient manner with a minimum of recovery time for the patient.

SUMMARY OF THE INVENTION

In an aspect, the present disclosure relates to an anchor assembly. The anchor assembly includes an anchor including a distal portion and a proximal portion, the anchor defining a cavity and an opening to the cavity; an insertion member disposed within the cavity of the anchor; and a sleeve coupled to the anchor, the sleeve disposed over the proximal portion of the anchor. In an embodiment, the distal portion of the anchor includes barbs. In another embodiment, the anchor includes a through hole. In yet another embodiment, the cavity includes threads. In a further embodiment, the insertion member includes a threaded proximal portion and a non-threaded distal portion. In yet a further embodiment, the insertion member includes a cannulation. In an embodiment, the sleeve includes a threaded proximal portion and a non-threaded distal portion. In another embodiment, the anchor includes protrusions.

In another aspect, the present disclosure relates to an anchor delivery device for tissue repair including a handle; a first knob coupled to the handle; a second knob coupled to the handle; and a shaft coupled to the handle, the shaft including an outer member, an inner member disposed within the outer member, and a driver disposed within the inner member. In an embodiment, a proximal portion of the driver is coupled to the first knob and a proximal portion of the outer member is coupled to the second knob. In another embodiment, the anchor delivery device further includes a sleeve coupled to the outer member, an anchor coupled to the inner member, and an insertion member disposed within a cavity of the anchor, the insertion member coupled to the driver.

Further features, aspects, and advantages of the present disclosure, as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings:

FIG. 2 shows a side view of the sleeve of the anchor assembly of FIG. 1.

FIG. 3 shows a cross-sectional view of the sleeve of FIG. 2.

FIG. 4 shows a side view of the anchor of the anchor assembly of FIG. 1.

FIG. 5 shows a cross-sectional view of the anchor of the anchor of FIG. 4.

FIG. 6 shows a cross-sectional view of the insertion member of the anchor assembly of FIG. 1.

FIG. 8 shows a cross-sectional view of the anchor delivery device of FIG. 7 prior to insertion of the anchor assembly into bone.

FIG. 9 shows an expanded view of the distal end of the shaft of the anchor delivery device of FIG. 8.

FIG. 10 shows a cross-sectional view of the anchor delivery device of FIG. 7 after insertion of the anchor assembly into bone.

FIG. 11 shows an expanded view of the distal end of the shaft of the anchor delivery device of FIG. 10.

FIG. 12 shows a side view of the anchor assembly of the present disclosure after the anchor assembly is placed within bone.

FIG. 13 shows a cross-sectional view of the anchor assembly of FIG. 12.

DETAILED DESCRIPTION OF THE EMBODIMENTS

Figure 1:
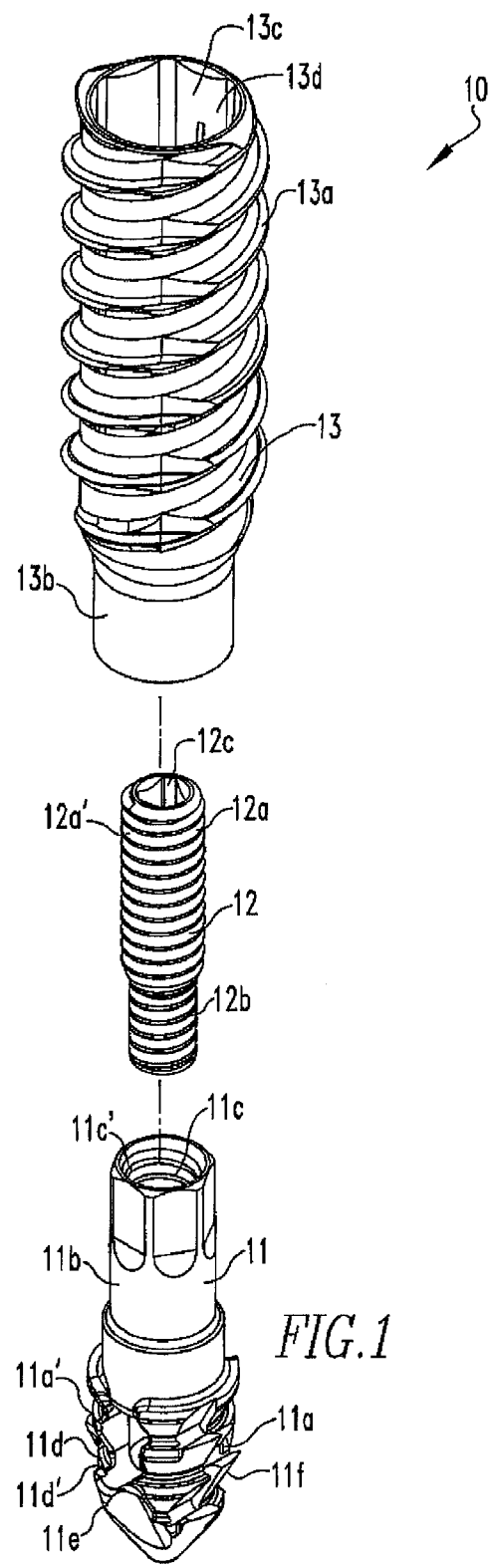
FIG. 1 shows an exploded view of the anchor assembly of the present disclosure.
Figure 7:
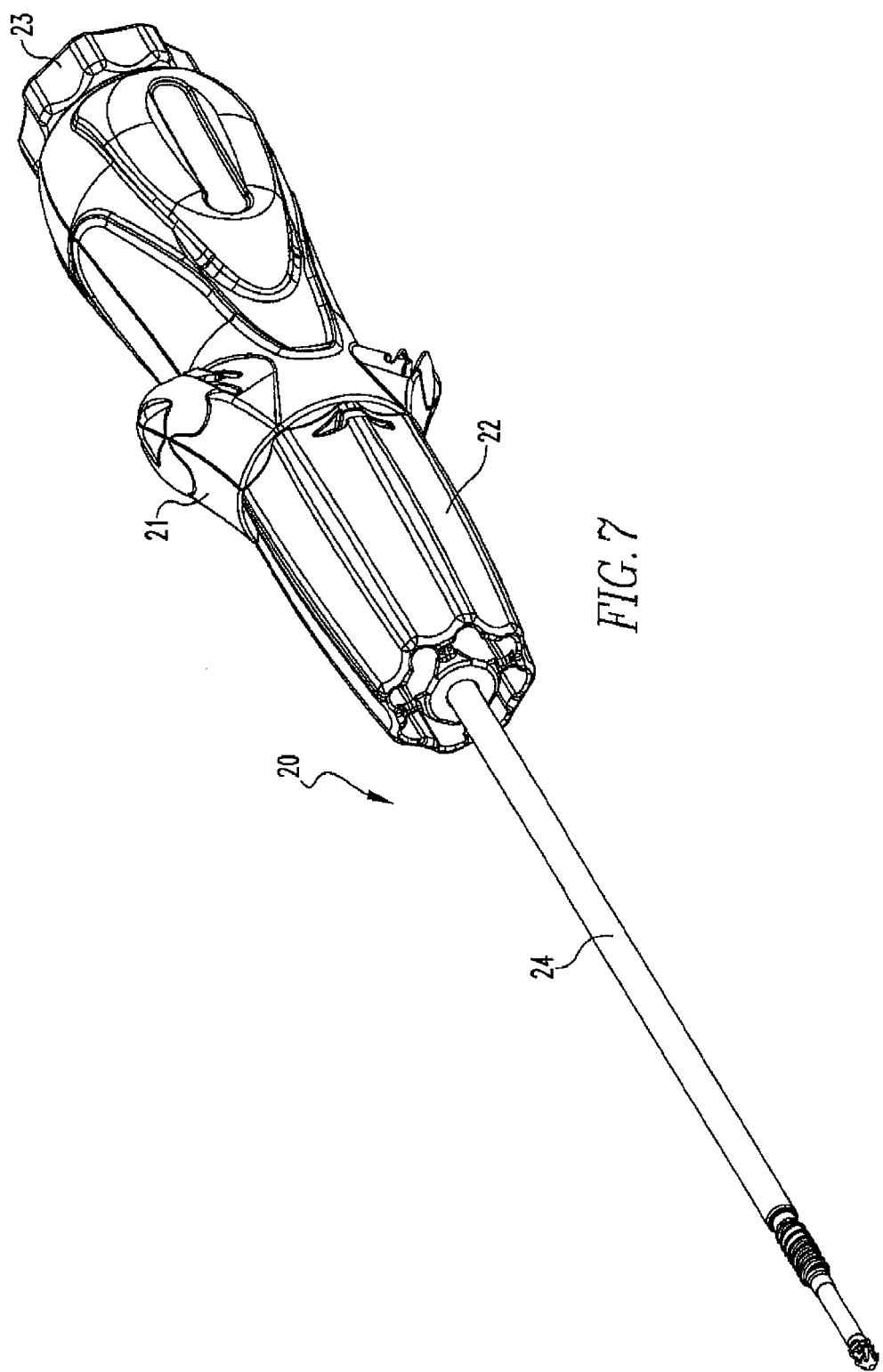
FIG. 7 shows an isometric view of the anchor delivery device of the present disclosure.

The embodiments were chosen and described in order to best explain the principles of the invention and its practical application to thereby enable others skilled in the art to best utilize the invention in various embodiments and with various modifications as are suited to the particular use contemplated.

FIGS. 1-6 show the components of the anchor assembly 10 of the present disclosure. The assembly 10 includes an anchor 11, an insertion member 12, and a sleeve 13. The anchor 11 includes a distal portion 11a, a proximal portion 11b, a cavity 11c defined within the anchor 11 and an opening 11c' to the cavity 11c, a through hole 11d having two openings 11d', protrusions 11e located below each opening 11d', and barbs 11f located on an outer surface 11a' of the distal portion 11a. The insertion member 12 includes a proximal portion 12a having threads 12a', a non-threaded distal portion 12b, and a cannulation 12c. The sleeve 13 includes a threaded proximal portion 13a, a non-threaded distal portion 13b, a cavity 13c, and an opening 13d to the cavity. The anchor cavity 11c includes threads 11c''' that engage threads 12a' of the insertion member 12 upon insertion of the member 12 into the cavity 11c.

FIGS. 7-11 show the delivery device 20 for use with the anchor assembly of FIG. 1. The device 20 includes a handle 21, a first knob 22 coupled to the handle 21, a second knob 23 coupled to the handle 21, and a shaft 24 coupled to the handle 21. The shaft 24 includes an outer member 24a, an inner member 24b disposed within the outer member 24a, and a driver 25 disposed within the inner member 24b.

As shown in FIGS. 8-11, the proximal portion 25a of the driver 25 is coupled to the first knob 23 and the proximal portion 26a of the outer member 24a is coupled to the second knob 22 via a movable member 27. The movable member 27 includes a distal portion 27a, a proximal portion 27b, and a cannulation 27c. The proximal portion 27b includes threads 27b' on its outer surface 27b". The movable member 27 is located in a cavity 21a of the handle 21. The cavity 21a includes a distal portion 21a' and a proximal portion 21a". The proximal portion 21a" includes threads 21b that engage the threads 27b' on the proximal portion outer surface 27b". As will be explained further below, due to the threaded engagement of the movable member 27 with the cavity proximal portion 21a", rotation of the knob 22 causes the outer member 24a to move axially along the length of the shaft 24. Rotation of the knob 22 is discontinued when an end 27a' of the movable member distal portion 27a engages an end 21c of the cavity distal portion 21a', thereby preventing over-insertion of the sleeve 13 into the bone.

A proximal portion 25a of the driver 25 includes threads 25a' that engage threads 29 on an inner surface 24b' of the inner member 24b. Threaded engagement of the driver 25 and inner member 24b allow for axial movement of the driver 25 along the shaft 24 via rotation of the knob 23. Rotation of the knob 23 is discontinued when a depth stop 25b engages an end 24b" of the inner member 24b, thereby preventing over-insertion of the insertion member 12 into the anchor 11, as will be further explained below.

During tissue repair, suture is attached to a soft tissue, a hole is created in bone, ends of the suture are placed through the through hole 11d of the anchor 11, the anchor 11 is placed within the bone hole via axial advancement of the delivery device 20, knob 23 is rotated to move the insertion member 12 axially and engage and fixate the suture to the anchor 11, and knob 22 is then rotated to move the sleeve 13 axially and place the distal end 13b of the sleeve 13 over the proximal end 11b of the anchor 11 and further lock the suture between the sleeve 13 and the bone. FIGS. 12 and 13 show the assembled anchor assembly 10 without the suture. The suture may be tensioned prior to advancing the insertion member 12 to engage the suture. Optionally, a suture anchor may be placed within bone, ends of the suture placed through the soft tissue, and the ends then placed through the through hole 11d of the anchor 11. Repair would continue as described above. A similar type of repair is shown and described in U.S. Patent Application Publication Nos. 20090112270, 20100016869, and 20100016902, the disclosures of which are incorporated herein by reference in their entireties.

The components of the anchor assembly are made from a polymer material and via an injection molding process. However, other materials and processes may be used. The handle and knobs of the delivery device are manufactured from a polymer material and via an injection molding process. The handle and knobs are coupled via an interference fit. However, other materials, processes of making, and methods of coupling may be used. The components of the shaft are made from a metal material via an extrusion or drawings process. The components of the shaft are coupled to the handle and knobs via a threaded fit or an interference fit. However, other materials, processes of making, and methods of coupling may be used.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. An anchor assembly comprising:
   an anchor comprising a distal portion and a proximal portion, the anchor defining a cavity therein, with a wall of the cavity having threads, and the anchor having an opening to the cavity located in the proximal anchor portion and a through hole defined in the distal portion;
   an insertion member, having a threaded proximal outer portion and a non-threaded distal outer portion, disposed within the cavity of the anchor, wherein the threaded proximal outer portion is engaged with the cavity wall threads, the non-threaded distal outer portion is disposed within the anchor cavity and a portion of the insertion member threaded portion extends from the anchor proximal portion; and
   a sleeve coupled to the anchor, the sleeve disposed about the proximal portion of the anchor and enclosing the insertion member extending from the anchor proximal portion,
   wherein the through hole defined in the distal portion of the anchor is not covered by the sleeve.

2. The anchor assembly of claim 1 wherein an outer surface of the distal portion of the anchor includes barbs.

3. The anchor assembly of claim 1 wherein the insertion member includes a cannulation.

4. The anchor assembly of claim 1 wherein the sleeve includes a threaded proximal outer portion and a non-threaded distal outer portion.

5. The anchor assembly of claim 4, wherein the non-threaded distal outer portion of the sleeve is coupled to the proximal portion of the anchor.

6. The anchor assembly of claim 1 wherein the anchor includes protrusions disposed about an outer surface of the distal portion.

7. An anchor assembly comprising:
   an anchor comprising a distal portion and a proximal portion, the anchor defining a threaded cavity having an opening located in the proximal anchor portion;
   an insertion member having a threaded proximal outer portion and a non-threaded distal outer portion, the threaded proximal outer portion configured to threadably engage with the anchor threaded cavity; and
   a sleeve having a proximal portion and a distal portion configured to couple about the proximal portion of the anchor,
   wherein a through-hole configured to receive a suture is provided in the anchor distal portion and
   wherein the sleeve is configured to not cover the through-hole in the anchor distal portion.

* * * * *